US011324913B2

(12) United States Patent
Bender, II et al.

(10) Patent No.: US 11,324,913 B2
(45) Date of Patent: May 10, 2022

(54) SYSTEMS AND METHODS FOR FILLING AN ANESTHESIA VAPORIZER USING AN ULLAGE VOLUME AND VENT

(71) Applicant: GE Precision Healthcare LLC, Wauwatosa, WI (US)

(72) Inventors: Thomas L. Bender, II, Madison, WI (US); Brady S. Weigel, Madison, WI (US); Herbert Caloud, Madison, WI (US); James N. Mashak, Sun Prairie, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 430 days.

(21) Appl. No.: 16/685,280

(22) Filed: Nov. 15, 2019

(65) Prior Publication Data

US 2021/0146088 A1    May 20, 2021

(51) Int. Cl.
  *A61M 16/18*    (2006.01)
  *B65D 47/24*    (2006.01)
  *A61M 39/26*    (2006.01)

(52) U.S. Cl.
  CPC .......... *A61M 16/183* (2013.01); *A61M 39/26* (2013.01); *B65D 47/248* (2013.01); *A61M 2039/268* (2013.01)

(58) Field of Classification Search
  CPC ................ A61M 16/183; A61M 39/26; A61M 2039/268; B65D 47/248
  See application file for complete search history.

(56) References Cited

U.S. PATENT DOCUMENTS

| 7,784,504 | B2 | 8/2010 | Freed et al. |
| 8,485,235 | B2 | 7/2013 | Cuzydlo |
| 8,522,839 | B2 | 9/2013 | Freed et al. |
| 8,528,550 | B2 | 9/2013 | Cuzyldo et al. |
| 9,186,478 | B2 | 11/2015 | Schnaars et al. |
| 10,406,313 | B2 | 9/2019 | Danielsen |

(Continued)

FOREIGN PATENT DOCUMENTS

| WO | 2007103658 A2 | 9/2007 |
| WO | 2008151667 A1 | 12/2008 |

(Continued)

OTHER PUBLICATIONS

Mills et al. Unpublished U.S. Appl. No. 15/987,720, filed May 23, 2018.

*Primary Examiner* — Jason K Niesz

(57) ABSTRACT

An anesthesia vaporizer system having a reservoir fillable with anesthetic agent from a bottle. A fill body defines a cavity that receives the anesthetic agent from the bottle via an inlet. The fill body further defines main and vent ports each communicating between the cavity of the fill body and the reservoir. A fill valve is receivable within the cavity of the fill body and moveable between open and closed positions. The anesthetic agent from the bottle flows through the inlet only when the fill valve is in the open position. A lower seal is receivable within the cavity of the fill body and moveable between open and closed positions by the fill valve. The vent port communicates between the cavity and the fill body only when the lower seal is in the open position. The lower seal is positionable in the open position when the fill valve is in the closed position.

20 Claims, 12 Drawing Sheets

(56) References Cited

U.S. PATENT DOCUMENTS

| | | | |
|---|---|---|---|
| 2004/0089375 A1* | 5/2004 | Falligant | A61M 16/183 141/351 |
| 2006/0048842 A1* | 3/2006 | Bunke | A61M 16/183 141/18 |
| 2010/0000958 A1 | 1/2010 | Mitchell et al. | |
| 2015/0320116 A1 | 11/2015 | Bleloch et al. | |
| 2016/0361514 A1 | 12/2016 | Warby | |
| 2017/0182281 A1 | 6/2017 | Kersey et al. | |
| 2017/0259026 A1 | 9/2017 | Mair et al. | |

FOREIGN PATENT DOCUMENTS

| | | |
|---|---|---|
| WO | 2010147843 A1 | 12/2010 |
| WO | 2016059038 A1 | 4/2016 |

* cited by examiner

SYSTEMS AND METHODS FOR FILLING AN ANESTHESIA VAPORIZER USING AN ULLAGE VOLUME AND VENT

FIELD

The present disclosure generally relates to systems and methods for filling an anesthesia vaporizer, and more particularly to systems and methods for filling an anesthesia vaporizer with overfill protection using an ullage volume with vents.

BACKGROUND

Anesthesia vaporizing systems (or vaporizers) are systems known in the art for vaporizing an anesthetic agent for delivery to a patient. The anesthetic agent is typically supplied to the system in liquid form, which the system then vaporizes for delivery to a patient as needed. These systems often also include ventilation functions to assist with breathing for the patient, whereby the vaporized anesthetic agent can then be introduced into the inspiratory side of the breathing circuit for delivery to the patient.

The following U.S. patents provide additional background information and are incorporated by reference in entirety: U.S. Pat. Nos. 7,784,504; 8,485,235; and 10,406,313.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to an anesthesia vaporizer system fillable with anesthetic agent from a bottle. A reservoir is configured to contain the anesthetic agent filled from the bottle. A fill body defines a cavity that receives the anesthetic agent from the bottle via an inlet. The fill body further defines a main port and a vent port each communicating between the cavity of the fill body and the reservoir. A fill valve is receivable within the cavity of the fill body and moveable between open and closed positions. The anesthetic agent from the bottle flows through the inlet only when the fill valve is in the open position. A lower seal is receivable within the cavity of the fill body and moveable between open and closed positions by the fill valve. The vent port communicates between the cavity and the fill body only when the lower seal is in the open position. The lower seal is positionable in the open position when the fill valve is in the closed position.

Another embodiment generally relates to an anesthesia vaporizer system fillable with anesthetic agent from a bottle. A reservoir is configured to contain the anesthetic agent filled from the bottle. A fill body defines a cavity that receives the anesthetic agent from the bottle via an inlet. The fill body further defines a main port and a vent port each communicating between the cavity of the fill body and the reservoir. A fill valve is receivable within the cavity of the fill body and axially translatable between open and closed positions. The anesthetic agent from the bottle flows through the inlet only when the fill valve is in the open position. A lower seal is receivable within the cavity of the fill body and axially compressible between open and closed positions by the fill valve. The lower seal comprises a blocking feature along an outer perimeter that selectively prevents flow through the vent port, where the anesthetic agent flows through the vent port only when the lower seal is in the open position. The lower seal is in the open position when the fill valve is in the closed position. The system is positionable in four positions, including: a first position in which the bottle valve is in the closed position, the fill valve is in the closed position, and the lower seal is in the open position; a second position in which the bottle valve is in the closed position, the fill valve is in the open position, and the lower seal is in the open position; a third position in which the bottle valve is in the closed position, the fill valve is in the open position, and the lower seal is in the closed position; and a fourth position in which the bottle valve is in the open position, the fill valve is in the open position, and the lower seal is in the closed position.

Another embodiment generally relates to an anesthesia vaporizer system fillable with anesthetic agent from a bottle. A reservoir is configured to contain the anesthetic agent filled from the bottle. A fill body defines a cavity that receives the anesthetic agent from the bottle via an inlet. The fill body further defines a main port and a vent port each communicating between the cavity of the fill body and the reservoir. A fill valve is receivable within the cavity of the fill body and moveable between open and closed positions. The anesthetic agent from the bottle flows through the inlet only when the fill valve is in the open position. A lower seal is receivable within the cavity of the fill body and moveable between open and closed positions by the fill valve. The anesthetic agent flows through the vent port only when the lower seal is in the open position. The lower seal is in the open position when the fill valve is in the closed position. The main port extends downwardly through an extension into the reservoir between upper and lower ends. An ullage volume is defined within the reservoir above the lower end of the extension, a cavity volume is defined as open space within the cavity surrounding the fill valve and the lower seal, and the ullage volume is greater than twice the cavity volume. The anesthetic agent flows into reservoir when the when the anesthetic agent in the reservoir is above the lower end of the extension only via the vent port.

Various other features, objects and advantages of the disclosure will be made apparent from the following description taken together with the drawings.

BRIEF DESCRIPTION OF THE DRAWINGS

The present disclosure is described with reference to the following Figures.

DETAILED DISCLOSURE

Anesthesia vaporizer systems are devices known in the medical field for safely and accurately administering anesthesia to a patient. These anesthesia vaporizers typically incorporate a reservoir for retaining anesthetic agent before the agent is vaporized for delivery to the patient, such as by incorporating within breathing tubes of a ventilator system. As the anesthetic agent within the reservoir is depleted, the anesthetic agent must be refilled from bottles, but must be done so in a safe manner that prevents spillage and other exposure, including both liquid and vaporized, of the anesthetic agent to the operator. The term anesthetic agent as used herein refers to all forms thereof (i.e., liquid, vapor, and gas).

The inventors have identified that for anesthesia vaporizer systems presently known in the art, "overfill" conditions are expected, but not sufficiently accommodated for by the system. Overfill occurs when a bottle containing anesthetic agent is used to fill the vaporizer, but the vaporizer reservoir reaches full capacity before the bottle is entirely drained. This full capacity is not necessarily the entire volume of the reservoir, which must be able to accommodate thermal expansion and the like. When the reservoir reaches full capacity, the inherent geometry within the bottle nozzle or bottle valve traps liquid and vapor anesthetic agent between the bottle and the vaporizer reservoir. This not only means that a portion of the anesthetic agent dispensed from the bottle cannot reach the reservoir where it can be used, but also provides an undesirable risk of exposure for the operator in that this portion of anesthetic agent also cannot be returned to the bottle.

The inventors have developed the presently disclosed systems and methods for managing this anesthetic agent trapped between the bottle and the reservoir, including through the incorporation of a multi-valve fill assembly. These systems and methods manage the liquid and gas exchange between the bottle and the reservoir, particularly by exploiting a ullage volume within the reservoir. This ullage volume may be designed to accommodate a desired amount of additional drainage according to the present disclosure, while still accommodating for thermal expansion, as discussed above. In this manner, the presently disclosed systems and methods not only provide for overfill protection to stop the flow of anesthetic agent from the bottle when the reservoir is full, but also ensure that essentially all of the anesthetic agent exiting the bottle is transferred to the reservoir.

Figure 1:
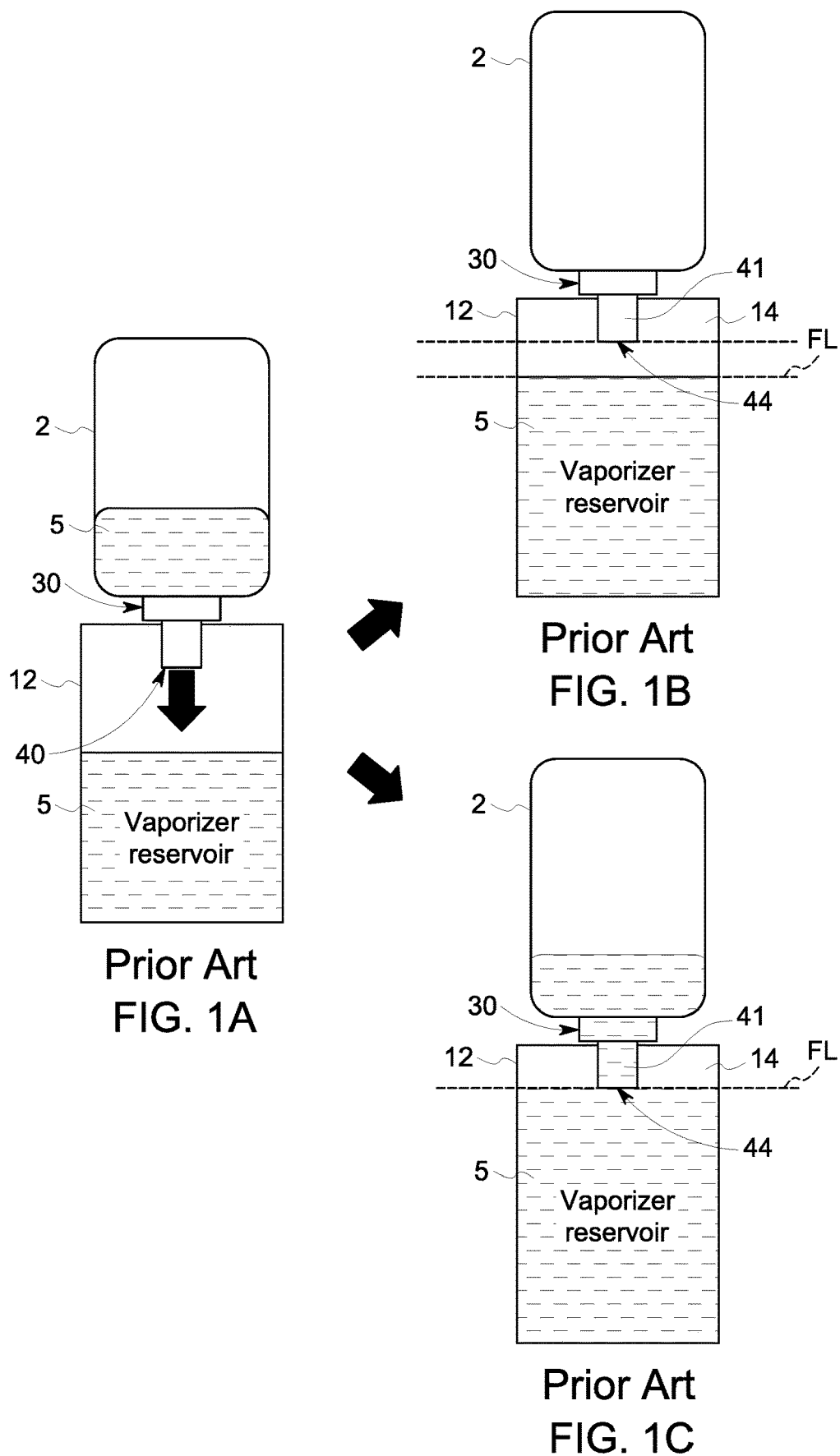
FIGS. 1A-1C schematically depict the filling of an anesthesia vaporizer as presently known in the art, including two drainage states depending on the fill level in the vaporizer reservoir.

FIGS. 1A-1C depict the filling process for systems and methods presently known in the art. FIG. 1A depicts the start of a fill process, whereby a bottle 2 containing anesthetic agent 5 is inserted into a fill body 30 leading to a reservoir 12 within the anesthesia vaporizing system. The anesthetic agent 5 from the bottle 2 drains through a main port 40 within the fill body 30 to fill up the reservoir 12. In the case in which the reservoir 12 has sufficient empty volume available to entirely empty the bottle 2, meaning that the fill level FL of liquid anesthetic agent 5 remains below a lower end 44 of the extension 41 from the main port 40, most of the anesthetic agent 5 from the bottle 2 may be drained into the reservoir 12 (FIG. 1B). However, in the situation shown in FIG. 1C, whereby there is insufficient room in to receive the entirety of the anesthetic agent 5 in the bottle 2, the fill level FL within the reservoir 12 reaches the lower end 44 of the extension 41 before the bottle 2 is entirely drained. When this occurs, the pressure differential between the anesthetic agent 5 in the bottle 2 and the anesthetic agent 5 in the reservoir 12 prevents the bottle 2 from entirely draining, and particularly results in anesthetic agent 5 being retained within the fill body 30. Once the bottle 2 is subsequently removed, this anesthetic agent 5 trapped within the fill body 30 remains until the next fill occurs.

The inventors have identified that the ullage volume 14 within the reservoir 12, the portion of volume above the lower end 44 of the extension 41, can be exploited to ensure drainage of the fill body 30, specifically through the incorporation of vent ports to be discussed below. Moreover, the systems and methods presently disclosed allow the filling of anesthetic agent 5 to be synchronized such that the ullage volume 14 is only fillable after the bottle 2 is no longer transferring anesthetic agent into the reservoir 12, which would otherwise eliminate the overfill protection necessary to prevent anesthetic agent from overflowing from the system.

Figure 2:
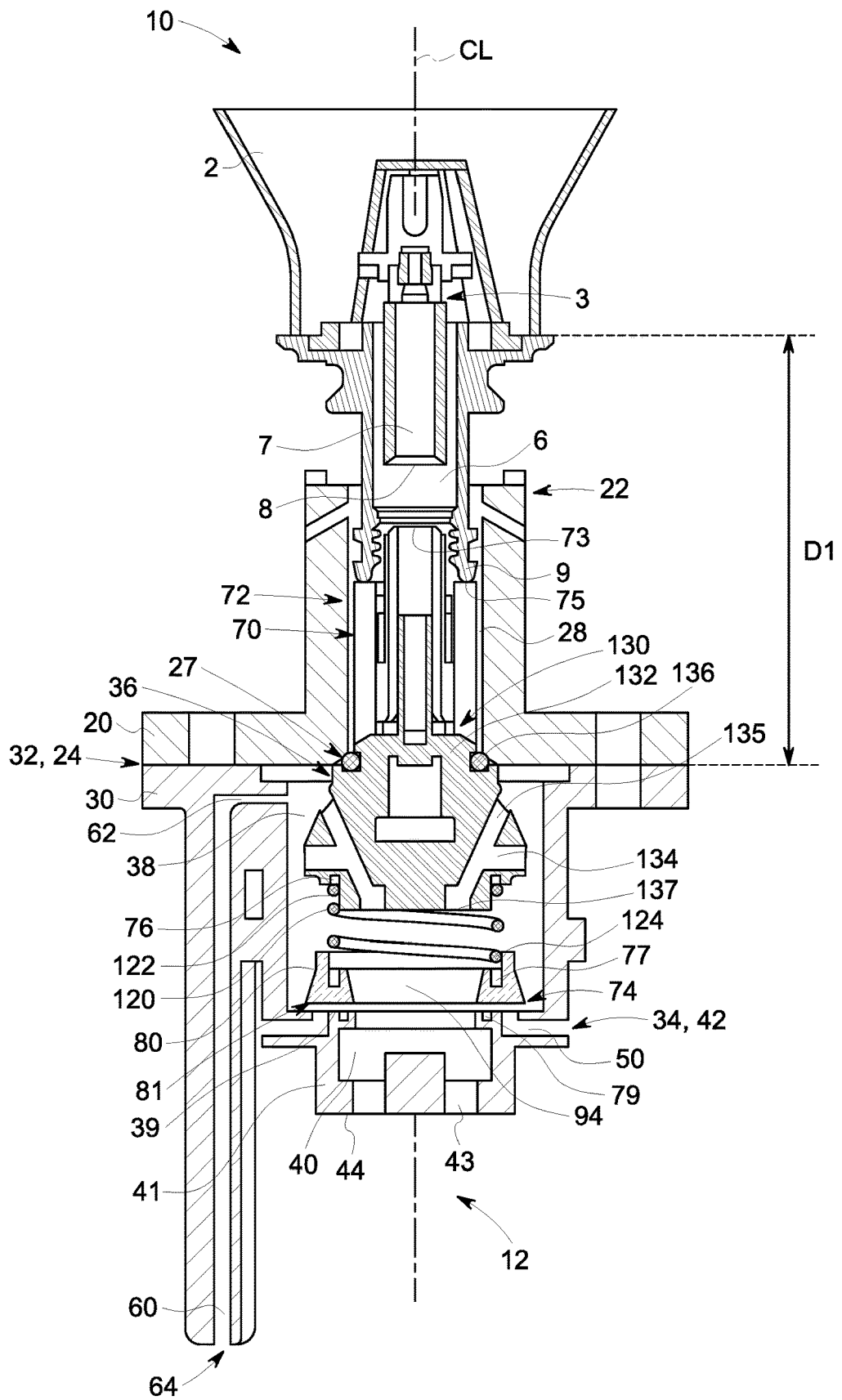
FIG. 2 is a front sectional view of one embodiment of a system for filling an anesthesia vaporizer according to the present disclosure.

FIG. 2 depicts an exemplary system 10 for filling anesthetic agent 5 from a bottle 2 into a reservoir 12 according to the present disclosure. The bottle 2 has a bottle valve 3 that controls the flow of the anesthetic agent through the opening 6 in the manner known in the art. In particular, the bottle valve 3 is actuated by providing a force on the base 8 of a plunger 7, whereby the force is applied by a bottle valve opening feature 73 and a fill valve 70 to be discussed further below. The bottle valve 3 of the present disclosure further includes feet 9 that exert a force on force receiving bases 75 of the fill valve 70. In this manner, downward forces on the bottle 2 not only cause opening of the bottle valve 3, but also translation of the fill valve 70.

The bottle 2 is shown inserted into a fill neck 20 that extends between an upper end 22 and a lower end 24, the lower end 24 being coupled to a fill body 30 of the anesthetic vaporizer system 10. The fill body 30 extends between an upper end 32 and a lower end 34 and defines a cavity 38 for receiving the anesthetic agent 5 from the bottle 2 via an inlet 36. The fill body 30 further defines a main port 40 that extends downwardly from a cavity base 39 of the cavity 38 through an extension 41 into the reservoir 12. The extension 41 has an upper end 42 and a lower end 44, whereby a passthrough 43 is defined within the lower end 44. The majority of the anesthetic agent 5 from a bottle 2 during a normal fill process will thereby travel through the bottle valve 3, through an opening 28 in the fill neck 20, through the inlet 36 of the fill body, into the cavity 38 of the fill body, and into the reservoir 12 of the anesthesia vaporizer system 10 via the main port 40.

The fill body 30 also defines a vent port 50 that communicates between the cavity 38 of the fill body 30 and the reservoir 12. As will be discussed further below, the vent port 50 allows for selectively filling the ullage volume 14 within the reservoir 12 to allow the cavity 38 of the fill body 30 to fully drain when anesthetic agent 5 is no longer flowing from the bottle 2. The fill body 30 also defines a gas exchange port 60 extending between an upper end 62 and a lower end 64, which allows gas to escape the reservoir 12 as anesthetic agent 5 is filled.

As previously discussed, the fill valve 70 is receivable within the cavity 38 of the fill body 30 and movable between open and closed positions. The fill valve 70 extends between an upper end 72 and a lower end 74 with a center line CL defined therebetween. In the embodiment shown, which depicts the fill valve 70 in a closed position, seals 136 provided with the upper member 130 of the fill valve 70 engage with an upper sealing surface 27 of the fill neck 20 such that anesthetic agent 5 cannot flow downwardly past the fill neck 20. In this manner, anesthetic agent 5 from the bottle 2 flows through the inlet 36 of the fill body 30 only when the fill valve 70 is in the open position.

As the fill valve 70 is moved downwardly by the bottle 2, anesthetic agent 5 is permitted to flow into the inlet 36 of the fill body 30 and into the cavity 38. In the embodiment shown, the upper member 130 of the fill valve 70 is a body 132 that defines a conduit 134 between an upstream end 135 and a downstream end 137. Anesthetic agent 5 may therefore flow through the conduit 134 to be directed downwardly toward the main port 40 at the cavity base 39 of the fill body 30. In certain embodiments, the fill valve 70 is moved against a biasing force provided by a biasing member 121 engaged between a lower end retainer 126 in the fill body 30 and upper end retainer 123 in the body 132 (see FIG. 8), A lower seal 80 is also receivable within the cavity 38 of the fill body 30, which is movable directly or indirectly by the upper member 130 of the fill valve 70. The lower seal 80 is also movable between open and closed positions, which as will become apparent selectively opens and closes the vent ports 50. Anesthetic agent 5 flows through the vent port 50 only when the lower seal 80 is in the open position. In certain embodiments, an additional lower seal 79, such as an O-ring, may be coupled to the cavity base 39 of the fill body 30 for providing a seal between the cavity base 39 and the lower seal 80.

The lower seal 80 defines an interior 94 and has a seal surface 81 at the lower end configured to seal with the cavity base 39 of the fill body 30. The interior 94 is provided in alignment with the main port 40 of the cavity 38 such that anesthetic agent 5 may be directed therethrough. In the embodiment shown, the lower seal 80 further defines a lower biasing device engagement feature 77 for engaging a lower end 124 of a biasing member 120. The biasing member 120 also engages at an opposite upper end 122 to an upper biasing device engagement feature 76 defined within the upper member 130. In this manner, the travel or force applied between the upper member 130 and the lower seal 80 by the biasing member 120 need not be the same as the biasing force of the biasing member 121 on the upper member 130 (FIG. 8), providing additional configurability in the sequential movements of valves.

The anesthetic vaporizer system 10 presently shown is positionable in at least four positions. In a first position, the bottle valve 3 is in a closed position, the fill valve 70 is in a closed position, and the lower seal 80 is in an open position. In this first position, anesthetic agent 5 is not permitted to flow out of the bottle 2, nor into the cavity 38. However, the lower seal 80 provides that any anesthetic agent 5 already within the fill body 30 and particularly the cavity 38 therein may exit the cavity 38 via the vent port 50. In a second position, the bottle valve 3 remains in the closed position, but the fill valve 70 moves to an open position while the lower seal 80 also remains in the open position. In this second position, anesthetic agent 5 is still prevented from flowing out of the bottle 2, but any anesthetic agent 5 within the fill neck 20 may now drain into the cavity 38 and into the reservoir 12 via the main port 40 or the vent port 50. In a third position, the bottle valve 3 remains in the closed position, the fill valve 70 remains in an open position, and the lower seal 80 is now in the closed position. Since the lower seal 80 is in the closed position, the vent ports 50 are thereby closed, preventing flow of anesthetic agent 5 therethrough. Finally, in a fourth position, the bottle valve 3 transitions to an open position to allow anesthetic agent 5 to flow out of the bottle 2. The fill valve 70 also remains in the open position, allowing this anesthetic agent 5 from the bottle 2 to flow into the cavity 38 of the fill body 30. Since the lower seal 80 remains in the closed position, this anesthetic agent is directed from the cavity 38 into the reservoir 12 via the main port 40.

As shown in FIG. 2, a bottle distance D1 is defined between the bottle 2 and the cavity 38 in the fill body 30. It will be recognized that the bottle distance D1 is reduced as force is applied on the bottle 2 in the downward direction toward the fill body 30. It will further be recognized that the four positions previously discussed are therefore sequential, transitioning from the first position to the fourth position progressively as the bottle 2 is pressed further towards the fill body 30, or in other words as the bottle distance D1 decreases.

As the fill process is completed and the bottle 2 is withdrawn, or in other words the bottle distance D1 is again increased, the positions follow in the reverse order. Essentially, the bottle valve 3 closes first, followed by the fill valve 70, and finally the lower seal 80 moves to the open position. However, there is a transition period in which the lower seal 80 and the fill valve 70 are both open, which allows the fill body 30 to drain before the bottle 2 is fully removed. The flow through the main port 40 automatically stops once the fill level FL in the reservoir 12 reaches the lower end 44 of the extension 41. This ensures that the anesthetic agent 5 is prevented from continuing to fill from the bottle 2, which would result in an overfill condition. However, this configuration also allows the remaining anesthetic agent 5 within the cavity 38 to drain via the main port 40 and/or the vent port 50 into the ullage volume 14 of the reservoir 12 by allowing the transfer of pressure (e.g., from the vapor in the ullage volume 14) to exchange with the liquid anesthetic agent 5 as a result of gravity and hydrodynamic pressure equalization. In this manner, the presently disclosed systems and methods allow for utilizing all of the anesthetic agent 5 while also improving the safety for the operator as discussed above.

Figure 3A:
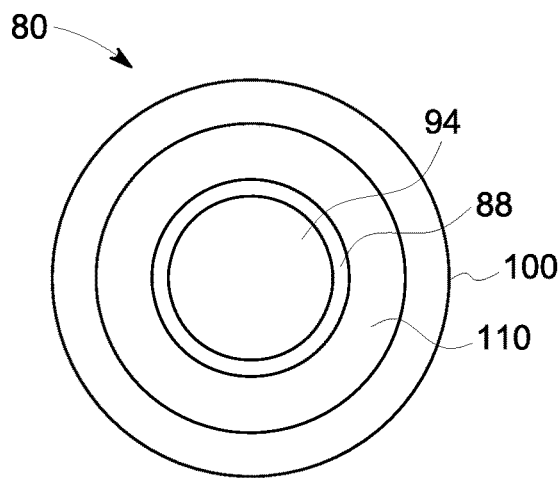
FIGS. 3A-3C are top, isometric, and bottom views of an exemplary lower seal for incorporating into alternate embodiments similar to that shown in FIG. 2.
Figure 3B:
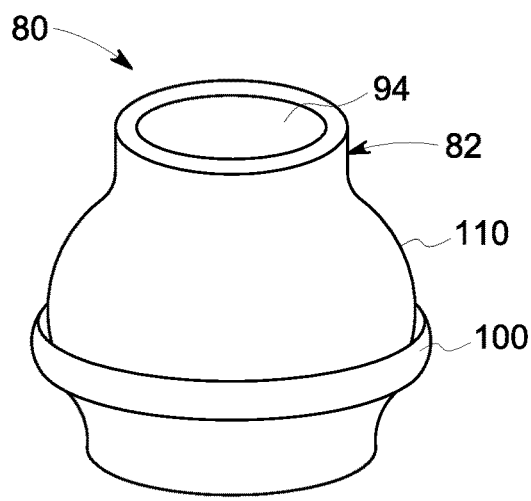
Figure 3C:
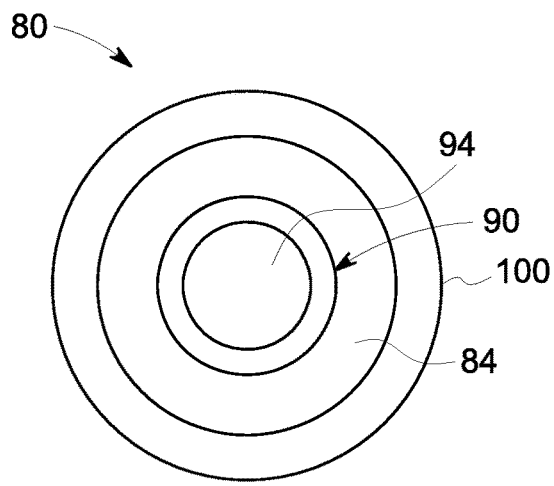

The resent inventors have developed several other configurations for anesthetic vaporizer systems 10, including some in which the lower seal 80 and biasing member 120 are incorporated together. As shown in FIGS. 3A-3C, another lower seal 80 is comprised of an elastomer (such as peroxide cured EPDM or platinum cured silicone, for example) and extends between an upper portion 82 and a lower portion 84 with a flex region 110 therebetween. As previously discussed, the lower seal 80 defines an interior 94 therein and, as will be discussed further below, includes a fill valve engagement lip 88 for engaging with the upper biasing device engagement feature 76 in the upper member 130, as well as a base portion 90 for sealingly engaging with the main port 40 of the fill body 30.

Figure 4:
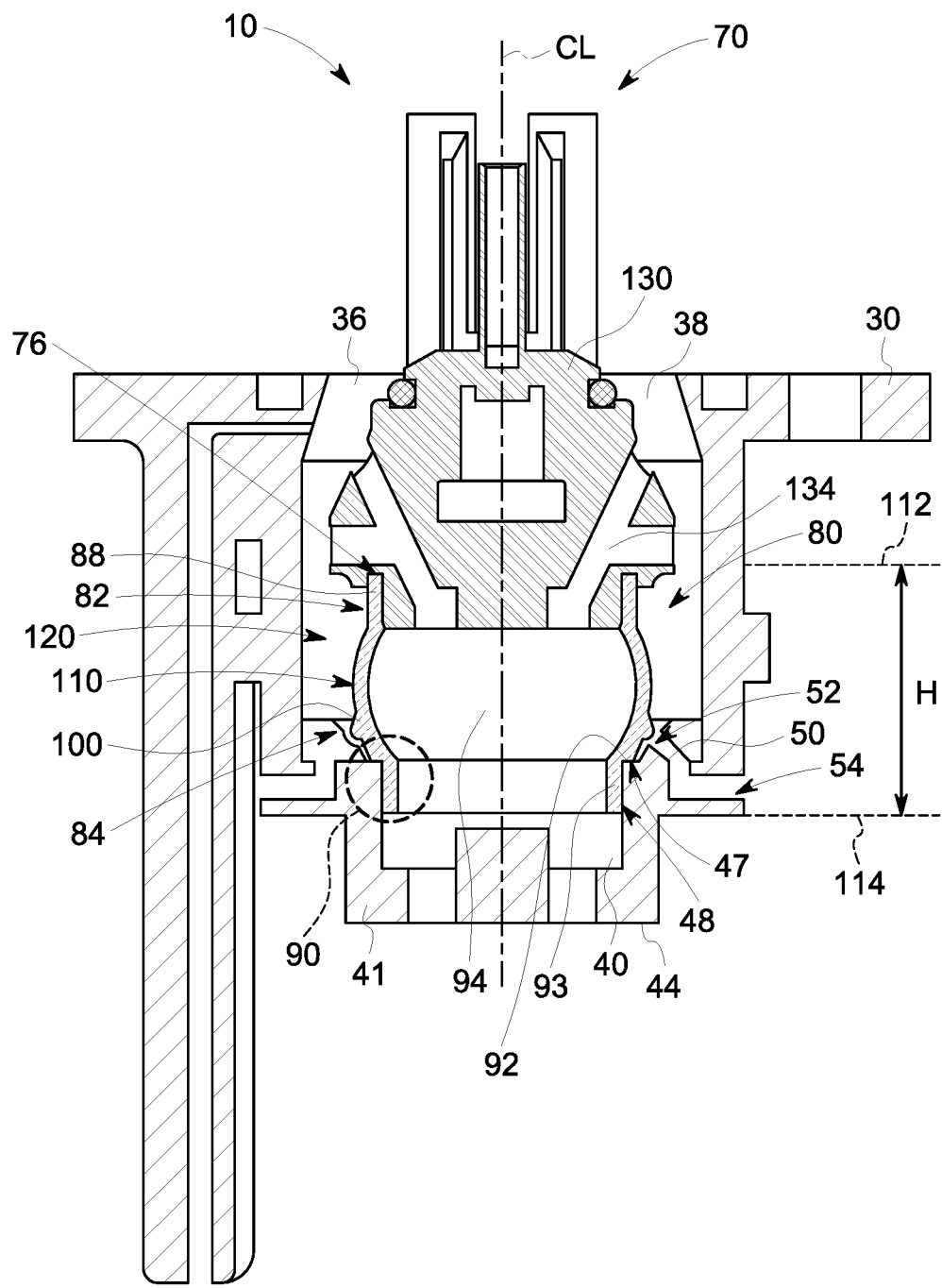
FIG. 4 is a front sectional view of another embodiment of a system according to the present disclosure incorporating the lower seal of FIGS. 3A-3C.
Figure 5:
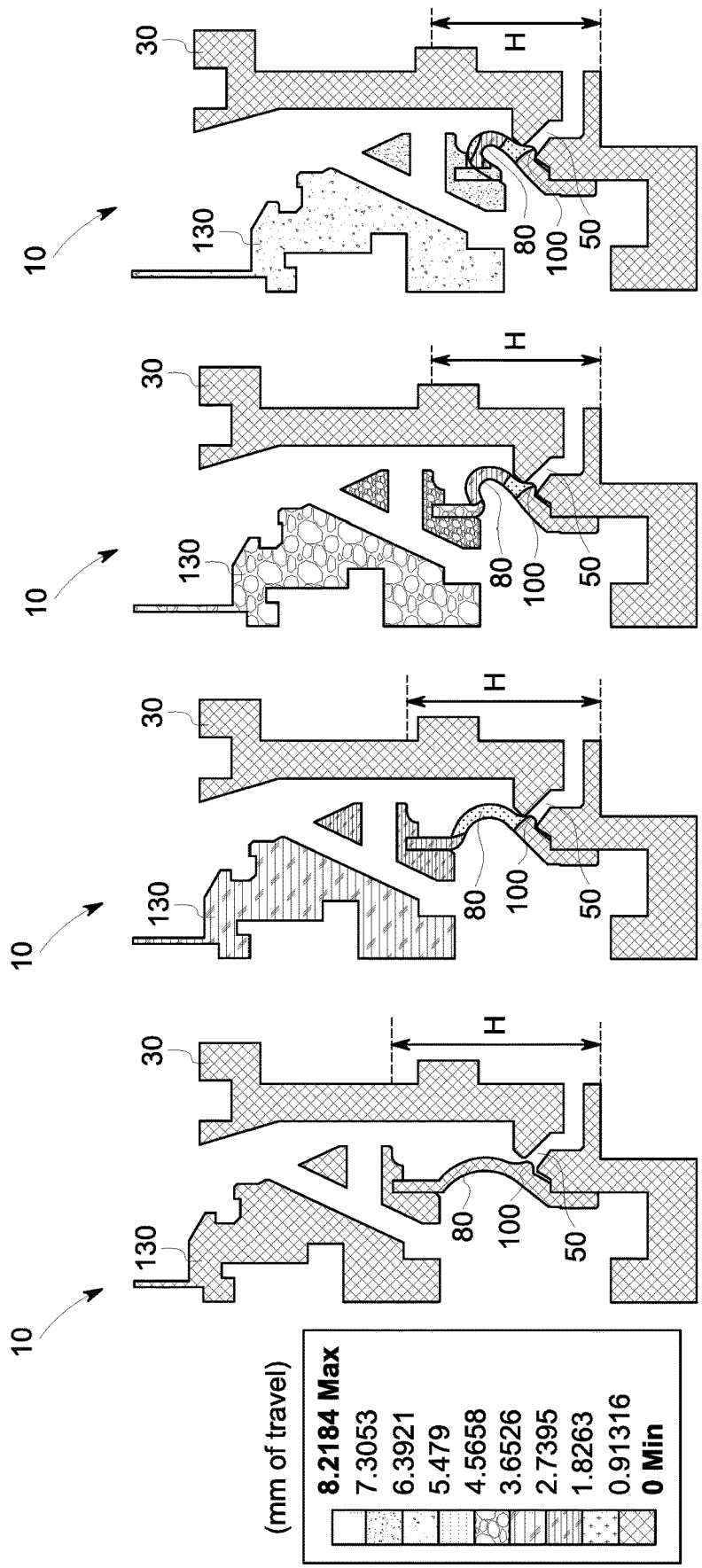
FIGS. 5A-5D are partial front view depictions of forces acting on the lower seal of FIGS. 3A-3C as incorporated within the system of FIG. 4 throughout the filling process.

FIG. 4 depicts the lower seal 80 of FIGS. 3A-3C incorporated within the fill valve 70 similar to that shown in FIG. 2. As shown, the lower seal 80 has a height H that reduces as the lower seal 80 is compressed by movement of the fill valve 70. In addition to providing upward biasing of the upper member 130 and this compressibility, it will be recognized that the flex region 110 of the lower seal 80 is configured to expand outwardly relative to the center line CL of the fill valve 70. In particular, the present embodiment includes a blocking feature 100 on the outer perimeter of the lower seal 80 within the flex region 110. The blocking feature 100 is provided in alignment with the vent port 50 to selectively close the vent port 50 as the lower seal 80 expands outwardly. In the embodiment shown, the vent port 50 extends between an upstream end 52 and a downstream end 54 and the blocking feature 100 is shaped to be receivable and sealingly block the upstream end 52.

Also shown in the embodiment of FIG. 4, which otherwise includes many of the functions described above with respect to FIG. 2, is a permanent engagement between the lower seal 80 and the main port 40. In particular, the present embodiment includes a main port 40 having a shelf 47 and a vertical portion 48 generally perpendicular thereto. Likewise, the lower seal 80 includes a shelf 92 and a vertical portion 93 within its base portion 90, which are configured to correspond to the shelf 47 and vertical portion 48 of the main port 40. In this manner, the lower seal 80 is provided in sealing engagement with the main port 40 such that anesthetic agent 5 may flow into the main port 40 only via the interior 94 of the lower seal 80. In other words, anesthetic agent 5 within the cavity 38 that is outside the lower seal 80, or not contained within the interior 94 thereof, may drain only via the vent port 50. As discussed above, draining via the vent port 50 is permitted only when the blocking feature 100 of the lower seal is not blocking the vent port 50, or in other words, in the closed position.

FIGS. 5A-5D depict measurement data collected for the lower seal 80 of FIGS. 3A-3C and FIG. 4 as the height H is compressed in operation. As can be seen, the blocking feature 100 progressively closes the vent port 50 as the lower seal 80 is compressed downwardly and expands outwardly. The geometry and dynamic movement of the lower seal 80 allows for different vent port 50 configurations and sizes to accommodate and optimize different anesthetic agents 5 and/or gas flow rates.

Figure 6:
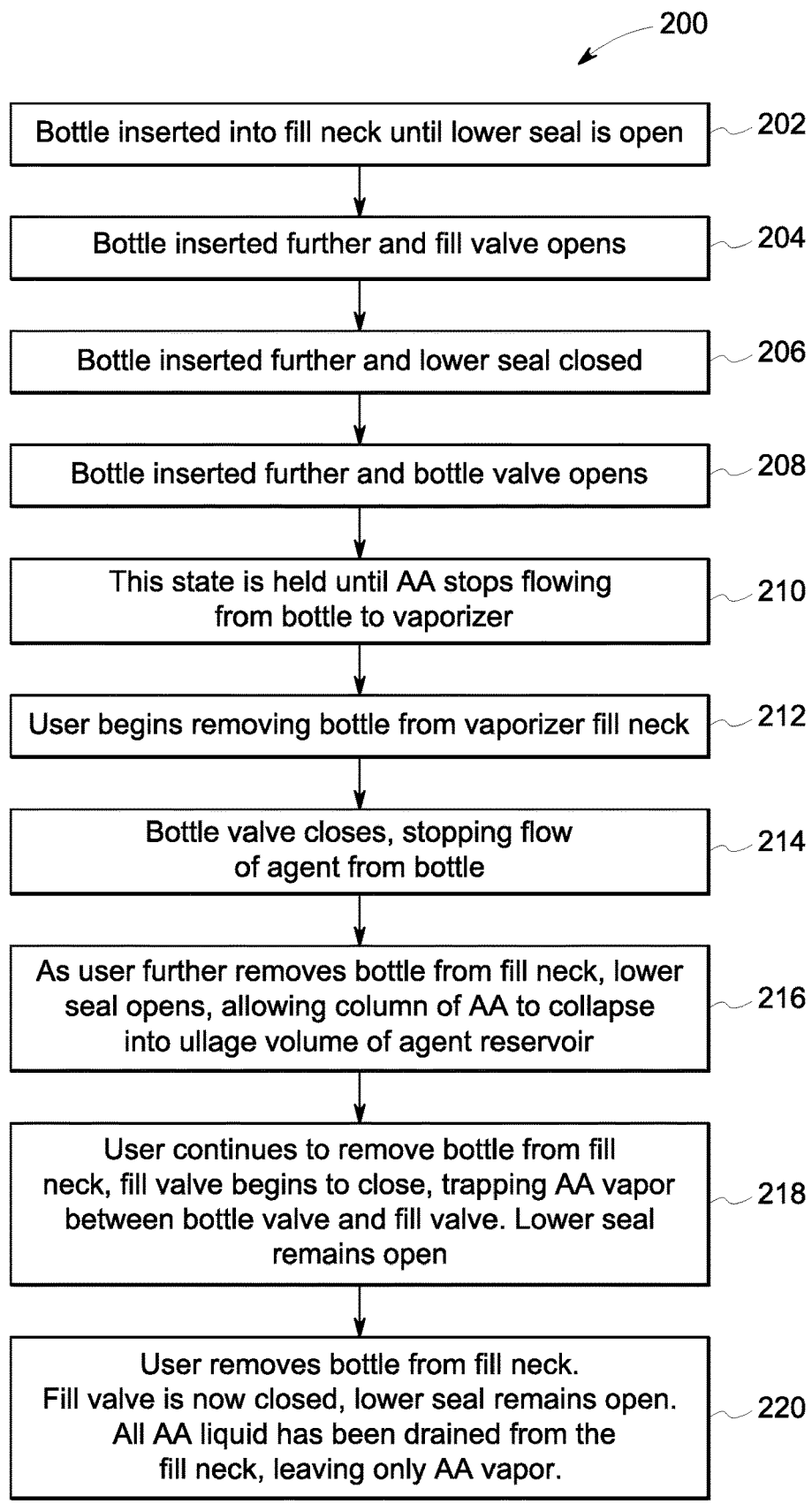
FIG. 6 is an exemplary process flow for filling an anesthesia vaporizer according to the present disclosure.

FIG. 6 generally depicts a process flow for filling anesthetic agent using the systems presently disclosed, including that previously shown in FIG. 4, for example. The method 200 begins with inserting the bottle 2 into the fill neck 20 until the lower seal 80 opens in step 202. The bottle 2 is then inserted further in step 204 until the fill valve 70 opens, and further until the lower seal closes in step 206. In step 208 the bottle 2 is further inserted and the bottle valve 3 opens, allowing anesthetic agent 5 to flow from the bottle 2. This state is then held in step 202 until the anesthetic agent 5 stops flowing from the bottle 2 into the anesthetic vaporizer system 10. The process may stop when the anesthetic agent 5 in the bottle 2 is depleted, or when the fill level FL within the reservoir 12 reaches the lower end 44 of the extension 41 of the main port 40 (see FIG. 1C). The user then begins withdrawing the bottle 2 from the vaporizer fill neck 20 in step 212, at which point the bottle valve 3 closes in step 214. In step 216, the user further removes the bottle 2 from the fill neck 20, whereby the lower seal 80 then opens, allowing a column of anesthetic agent 5 to collapse into the ullage volume 14 of the reservoir 12 via the vent port 50. In step 218 the user continues to remove the bottle 2 from the fill neck 20, at which point the fill valve 70 begins to close, trapping an anesthetic agent 5 vapor between the bottle valve 3 and the fill valve 70. The lower seal 80 remains open, allowing any further anesthetic agent 5 within the cavity 38 to drain into the ullage volume 14 of the reservoir 12. Finally, in step 220 the user removes the bottle 2 from the fill neck 20, whereby the fill valve 70 is now closed, the lower seal 80 remains open, and all anesthetic agent 5 has been drained from the fill neck 20, leaving only anesthetic agent 5 vapor.

Figure 7:
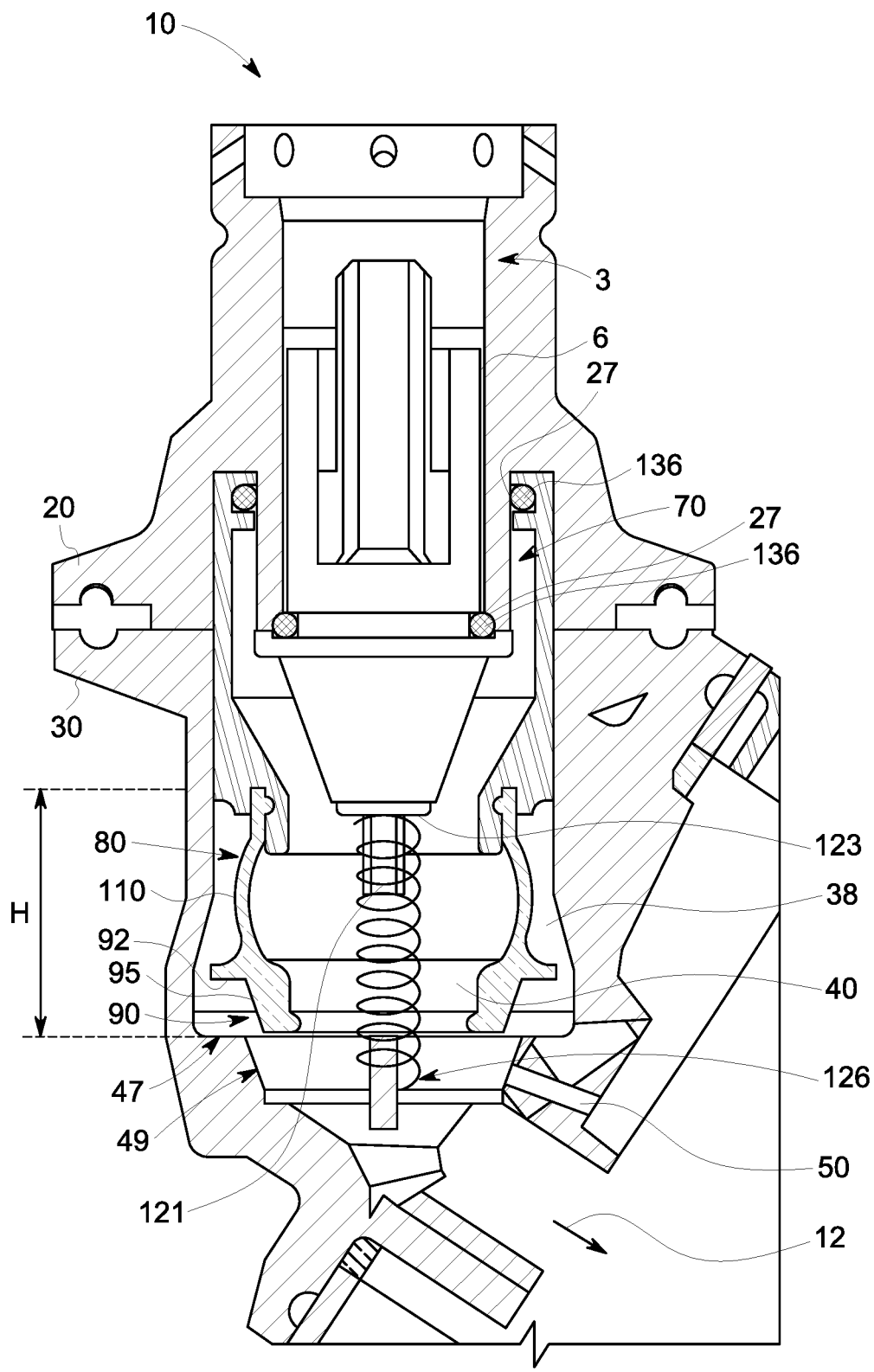
FIG. 7 is a partial sectional front view of another embodiment of a system according to the present disclosure.
Figure 8:
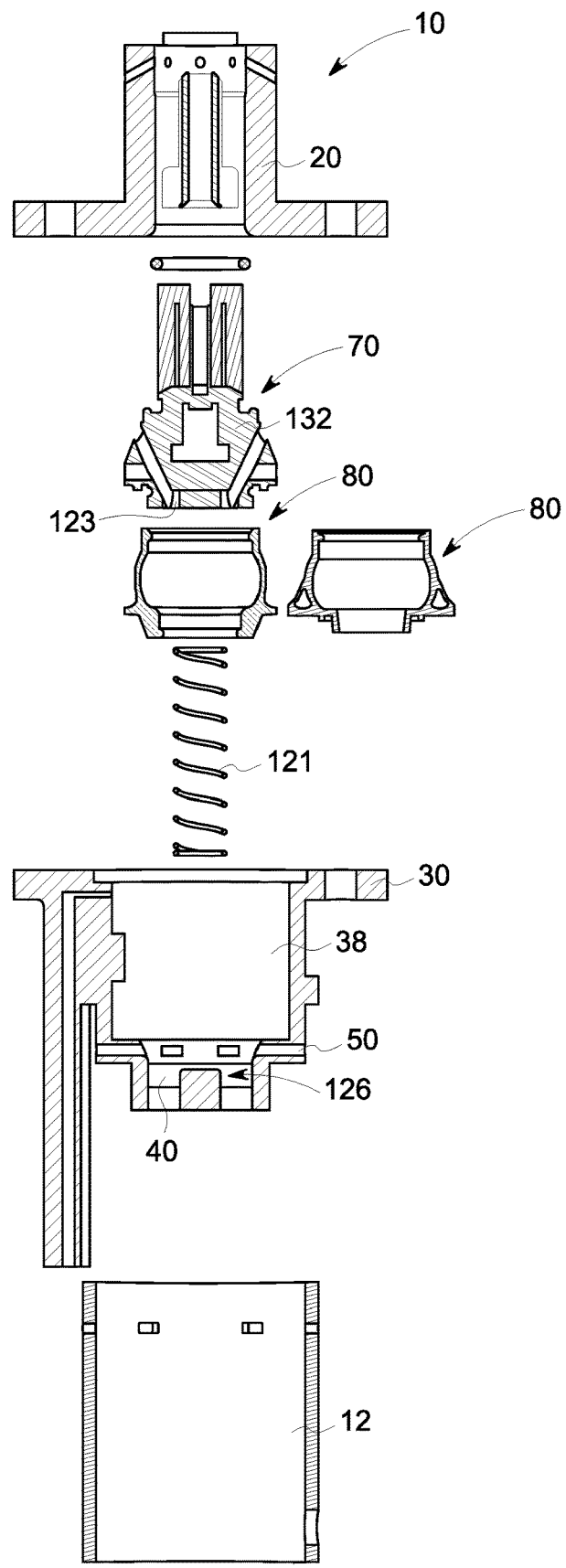
FIG. 8 is an exploded sectional front view of another embodiment of a system according to the present disclosure, shown with two examples of lower seals.

Further embodiments have also been developed by the inventors that generally function in a similar manner to that previously described. In the embodiments of FIGS. 7 and 8, the base portion 90 of the lower seal 80 now has an angled portion 95 in place of the vertical portion 93 shown in FIG. 4. The inventors have identified that providing an angled portion 95, along with the corresponding angled portion 49 and the main port 40, is particularly advantageous in providing a self-centering, durable, and effective seal between the lower seal 80 and the fill body 30. In the embodiment shown, the lower seal 80 still includes a shelf 92 for engagement with the shelf 47 of the main port 40. However, it should be recognized that this shelf 92 is not required. In the embodiment of FIG. 7, in contrast to that shown in FIG. 8, the anesthetic vaporizer system 10 is configured such that the reservoir 12 is not directly below the cavity 38, allowing different locations for positioning the fill body 30 and fill neck 20 relative to the reservoir 12.

Figure 9:
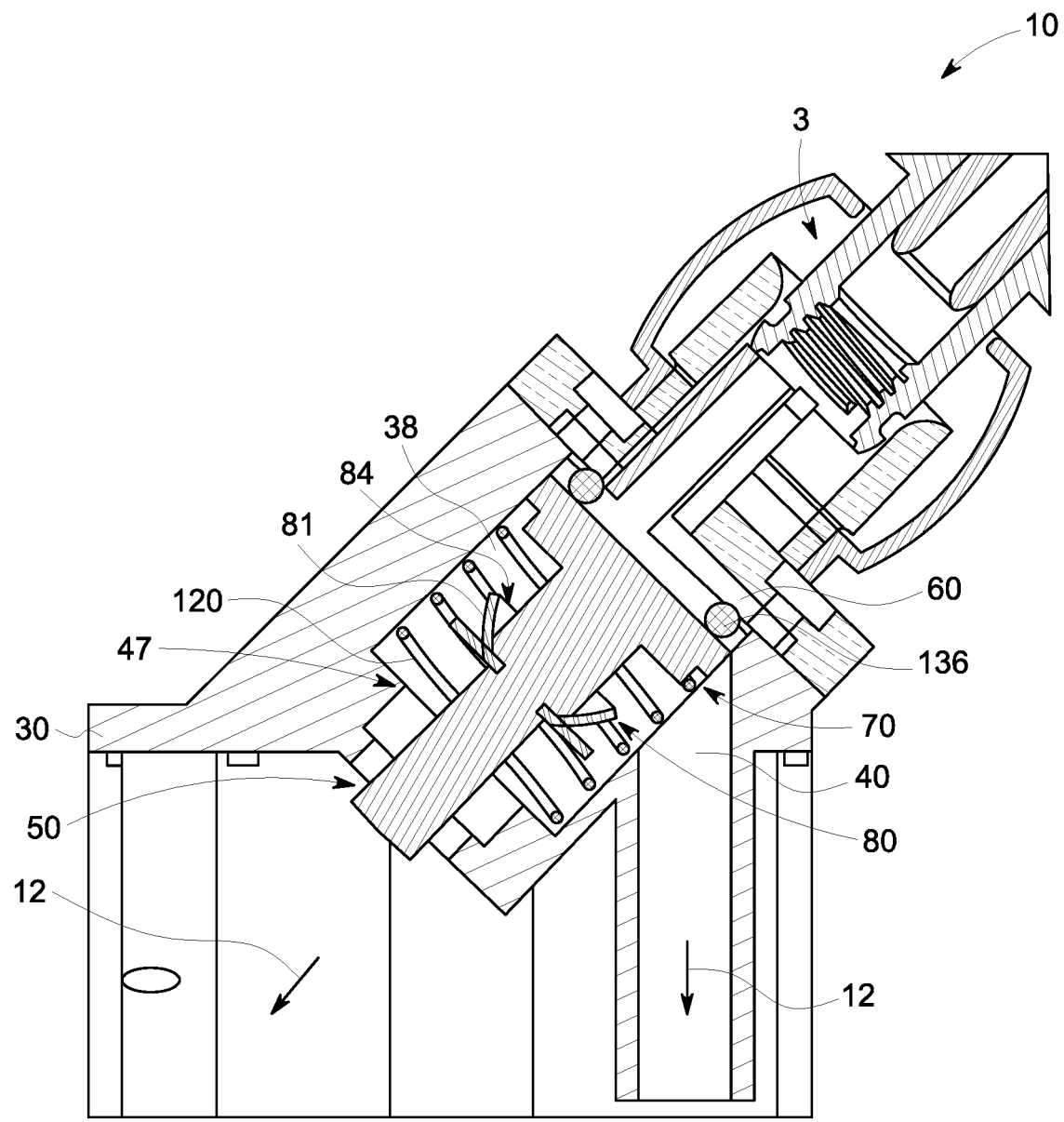
FIG. 9 is a partial sectional front view of another embodiment of a system according to the present disclosure.

Another configuration in which the cavity 38 of the fill body 30 is not provided directly above the reservoir 12 is shown in FIG. 9. In this embodiment, the main port 40 is shown to be upstream of the vent port 50, whereby the anesthetic agent 5 no longer flows through an interior 94 of the lower seal 80 to flow through the main port 40 to the reservoir 12. In this configuration, the lower seal 80 does not define an interior 84 at all, but provides venting via the vent port 50 through selective engagement of the seal surface 81 in a similar manner to that previously discussed. This configuration provides for separation of the liquid and gas (or vapor) exchange. In certain embodiments, the seal surface 81 is a flexible washer that seals on its inner diameter against the moving fill valve 70, and between the face of the seal surface 81 and the shelf 47 of the cavity 38. The washer may be an elastomer such as EPDM or silicone, for example.

Figure 10:
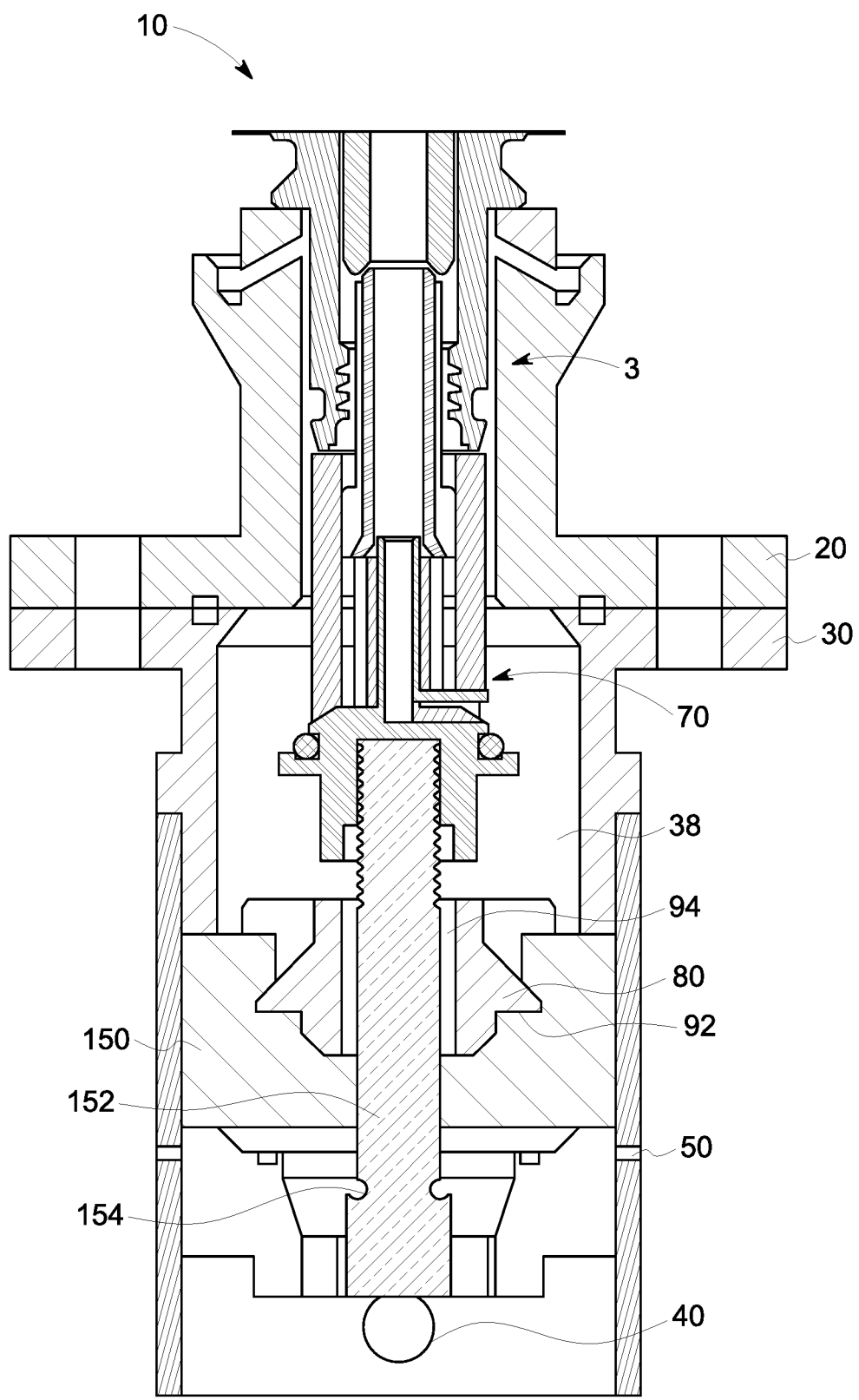
FIG. 10 is a partial sectional front view of another embodiment of a system according to the present disclosure.

FIG. 10 depicts a further embodiment according to the present disclosure, now including a movable piston 150. The piston 150 selectively blocks the vent ports 50 as it is moved downwardly. A blocker 152 is also translated downwardly with the piston 150, whereby the blocker 152 defines one or more openings 154. When the openings 154 are in alignment with the main port 40, anesthetic agent 5 is permitted to flow through the interior 94 of the lower seal 80, and through the openings 154 into the main port 40. Biasing members, such as the biasing member 120 previously discussed and shown in FIG. 2, may be incorporated to bias the fill valve 70 into the closed position.

Figure 11:
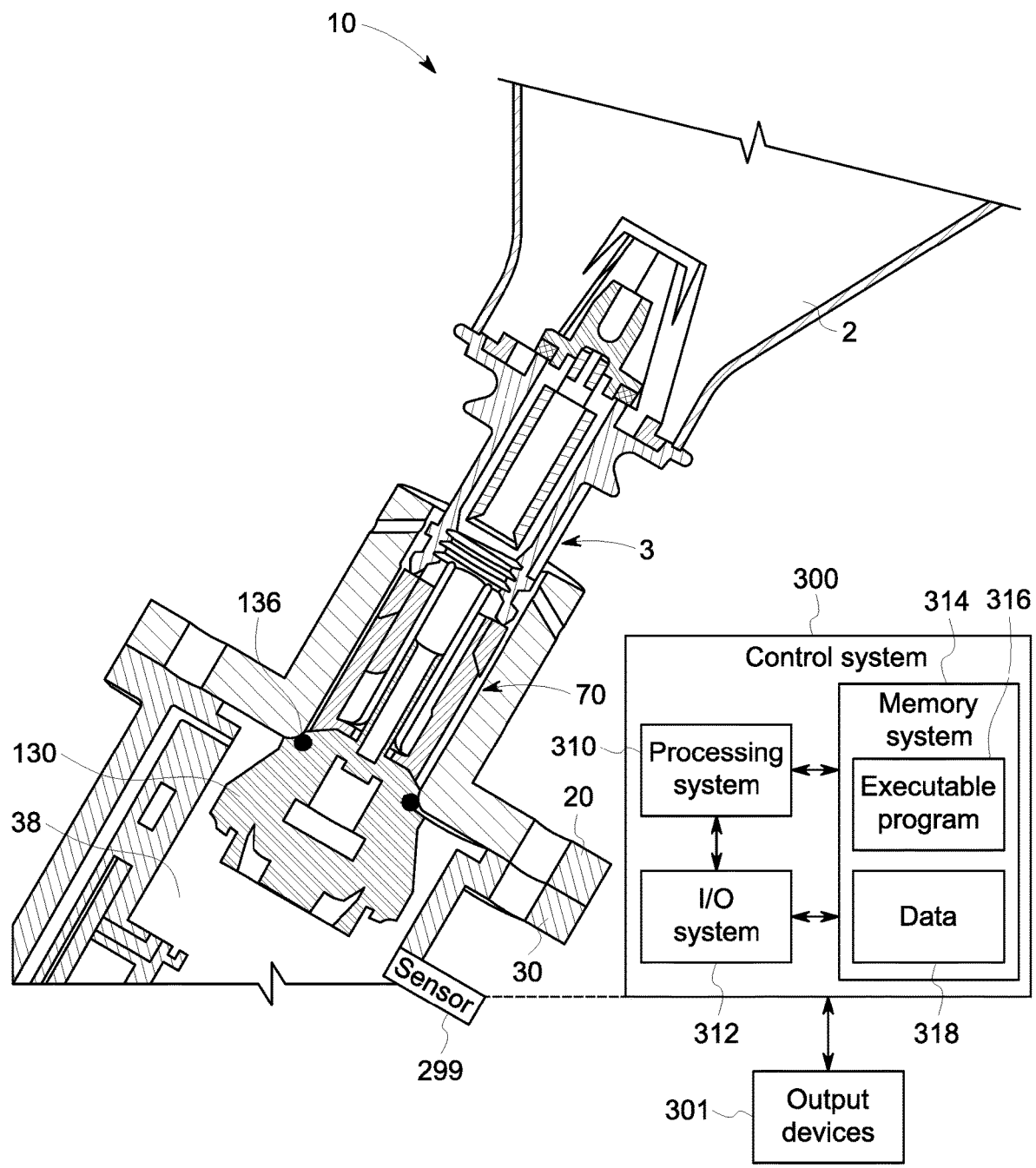
FIG. 11 is a partial sectional front view of another embodiment of a system according to the present disclosure, now incorporating a sensor for detecting a filling state.
Figure 12:
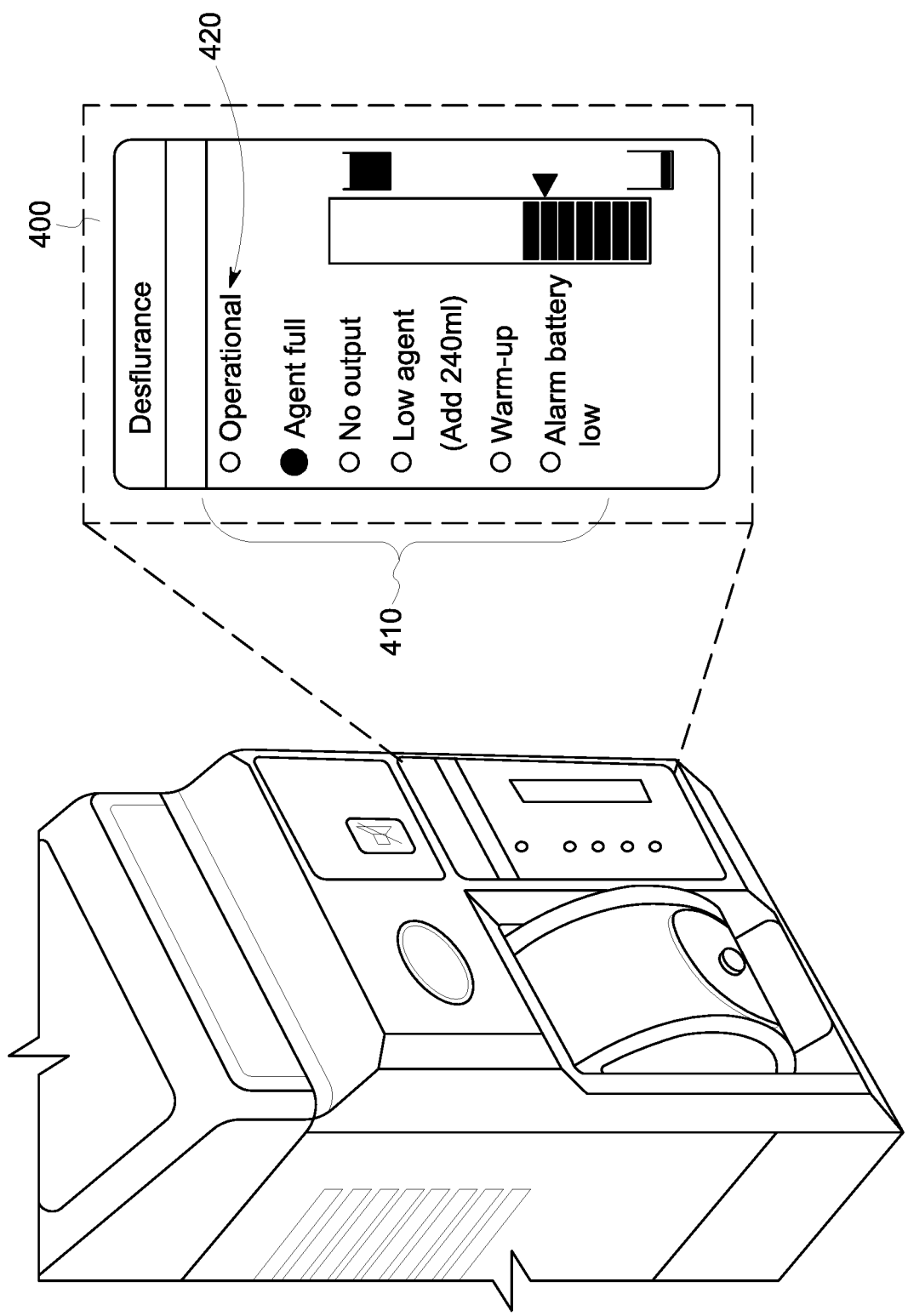
FIG. 12 depicts a front view of an exemplary display for providing the fill state such as detected in the system of FIG. 11.

FIGS. 11 and 12 depict an embodiment of an anesthetic vaporizer system 10 similar to that shown in FIGS. 2 and 4, but now incorporating a sensor 299 for detecting the position of the fill valve 70, thereby indicating a fill state for the system 10. The state of the fill valve 70 as determined by the sensor 299 may be further provided to the user via a display 400 on the front of the anesthetic vaporizer device. In the embodiment shown, the display 400 includes indicators 410 relating to the fill level of the anesthetic agent 5 within the reservoir 12. In addition, one of the indicators 410 includes the operational state 420 of the device. If the sensor 299 detects that the fill valve 70 is in a filling position, the operational state 420 shows that the system is not presently operational, which could harm the machine or place the operator at risk of exposure. In addition to providing this indication on the display 400, the sensor 299 may be operatively connected to various operations of the ventilator system, such as preventing the anesthetic vaporization process if the sensor 299 determines that the fill process is in progress.

An exemplary control system 300 for controlling the system 10, including through inputs received from the sensor 299, is shown in FIG. 11. Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

The control system 300 may be a computing system that includes a processing system 310, memory system 314, and input/output (I/O) system 312 for communicating with other devices, such as input devices 99 and output devices 301. The processing system 310 loads and executes an executable program 316 from the memory system 314, accesses data 318 stored within the memory system 314, and directs the system 10 to operate as described in further detail below.

The processing system 310 may be implemented as a single microprocessor or other circuitry, or be distributed across multiple processing devices or sub-systems that cooperate to execute the executable program 316 from the memory system 314. Non-limiting examples of the processing system include general purpose central processing units, application specific processors, and logic devices.

The memory system 314 may comprise any storage media readable by the processing system 310 and capable of storing the executable program 316 and/or data 318. The memory system 314 may be implemented as a single storage device, or be distributed across multiple storage devices or sub-systems that cooperate to store computer readable instructions, data structures, program modules, or other data. The memory system 314 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. An anesthesia vaporizer system fillable with anesthetic agent from a bottle, the system comprising:
   a reservoir configured to contain the anesthetic agent filled from the bottle;
   a fill body defining a cavity that receives the anesthetic agent from the bottle via an inlet, wherein the fill body further defines a main port and a vent port each communicating between the cavity of the fill body and the reservoir;
   a fill valve receivable within the cavity of the fill body and moveable between open and closed positions, wherein the anesthetic agent from the bottle flows through the inlet only when the fill valve is in the open position; and
   a lower seal receivable within the cavity of the fill body and moveable between open and closed positions by the fill valve, wherein the vent port communicates between the cavity and the fill body only when the lower seal is in the open position;
   wherein the lower seal is positionable in the open position when the fill valve is in the closed position.

2. The system according to claim 1, the fill valve is axially translatable between the open and closed positions.

3. The system according to claim 1, wherein the lower seal is coupled to the fill valve via a biasing member that biases the lower seal away from the fill valve.

4. The system according to claim 1, wherein the system is configured such that when the reservoir is full any of the anesthetic agent that flowed out of the bottle remains outside of the bottle.

5. The system according to claim 1, wherein the lower seal has a height and is axially compressible such that the height is less in the open position than in the closed position.

6. The system according to claim 5, wherein the lower seal has a blocking feature having a width, wherein the blocking feature prevents the anesthetic agent from flowing through the vent port when in the closed position, and wherein the width of the blocking feature is greater in the closed position than in the open position.

7. The system according to claim 1, wherein the bottle has a bottle valve that is moveable between open and closed positions, wherein in the closed position the anesthetic agent is prevented from flowing out of the bottle, further comprising a bottle opening feature that moves the bottle valve from the closed position to the open position when the bottle moves towards the cavity in the fill body.

8. The system according to claim 7, wherein the system is positionable in four positions that comprise:
a first position in which the bottle valve is in the closed position, the fill valve is in the closed position, and the lower seal is in the open position;
a second position in which the bottle valve is in the closed position, the fill valve is in the open position, and the lower seal is in the open position;
a third position in which the bottle valve is in the closed position, the fill valve is in the open position, and the lower seal is in the closed position; and
a fourth position in which the bottle valve is in the open position, the fill valve is in the open position, and the lower seal is in the closed position.

9. The system according to claim 8, wherein a distance between the bottle and the cavity in the fill body varies in each of the four positions, and wherein reducing the distance causes the system to move from the first position, then to the second position, then to the third position, and then to the fourth position.

10. The system according to claim 1, wherein the main port extends downwardly through an extension into the reservoir between upper and lower ends, and wherein the system is configured such that the anesthetic agent flows into the reservoir via the main port only when the anesthetic agent in the reservoir is below the lower end of the extension.

11. The system according to claim 10, wherein the system is configured such that the anesthetic agent flows into the reservoir when the anesthetic agent in the reservoir is above the lower end of the extension.

12. The system according to claim 11, wherein an ullage volume is defined within the reservoir above the lower end of the extension, wherein a cavity volume is defined as open space within the cavity surrounding the fill valve and the lower seal, and ullage volume is greater than the cavity volume.

13. The system according to claim 12, wherein the ullage volume is greater than twice the cavity volume.

14. The system according to claim 1, wherein the lower seal is annular and defines an interior between an upper portion and a lower portion, wherein the lower portion is sealingly receivable within the main port of the fill body such that the anesthetic agent in the cavity flows through the main port only via the interior of the lower seal.

15. The system according to claim 14, wherein the lower portion of the lower seal is conically shaped.

16. The system according to claim 15, wherein the main port is conically shaped to correspond to the lower portion of the lower seal.

17. The system according to claim 14, wherein the lower seal comprises an elastomeric material.

18. The system according to claim 17, wherein the elastomeric material comprises at least one of EPDM and silicone.

19. An anesthesia vaporizer system fillable with anesthetic agent from a bottle, the system comprising:
a reservoir configured to contain the anesthetic agent filled from the bottle;
a fill body defining a cavity that receives the anesthetic agent from the bottle via an inlet, wherein the fill body further defines a main port and a vent port each communicating between the cavity of the fill body and the reservoir;
a fill valve receivable within the cavity of the fill body and axially translatable between open and closed positions, wherein the anesthetic agent from the bottle flows through the inlet only when the fill valve is in the open position; and
a lower seal receivable within the cavity of the fill body and axially compressible between open and closed positions by the fill valve, wherein the lower seal comprises a blocking feature along an outer perimeter that selectively prevents flow through the vent port, wherein the anesthetic agent flows through the vent port only when the lower seal is in the open position;
wherein the lower seal is in the open position when the fill valve is in the closed position; and
wherein the system is positionable in four positions, including:
a first position in which the bottle valve is in the closed position, the fill valve is in the closed position, and the lower seal is in the open position;
a second position in which the bottle valve is in the closed position, the fill valve is in the open position, and the lower seal is in the open position;
a third position in which the bottle valve is in the closed position, the fill valve is in the open position, and the lower seal is in the closed position; and
a fourth position in which the bottle valve is in the open position, the fill valve is in the open position, and the lower seal is in the closed position.

20. An anesthesia vaporizer system fillable with anesthetic agent from a bottle, the system comprising:
a reservoir configured to contain the anesthetic agent filled from the bottle;
a fill body defining a cavity that receives the anesthetic agent from the bottle via an inlet, wherein the fill body further defines a main port and a vent port each communicating between the cavity of the fill body and the reservoir;
a fill valve receivable within the cavity of the fill body and moveable between open and closed positions, wherein the anesthetic agent from the bottle flows through the inlet only when the fill valve is in the open position; and
a lower seal receivable within the cavity of the fill body and moveable between open and closed positions by the fill valve, wherein the anesthetic agent flows through the vent port only when the lower seal is in the open position;
wherein the lower seal is in the open position when the fill valve is in the closed position; and
wherein the main port extends downwardly through an extension into the reservoir between upper and lower ends, wherein an ullage volume is defined within the reservoir above the lower end of the extension, wherein a cavity volume is defined as open space within the cavity surrounding the fill valve and the lower seal, wherein the ullage volume is greater than twice the cavity volume, and where the anesthetic agent flows into reservoir when the when the anesthetic agent in the reservoir is above the lower end of the extension only via the vent port.

* * * * *